United States Patent [19]
Inagi et al.

[11] Patent Number: 5,618,799
[45] Date of Patent: Apr. 8, 1997

[54] POWDER PREPARATION FOR HEALING DAMAGED SKIN

[75] Inventors: Toshio Inagi, Mishima; Saibi Suehiro, Numazu, both of Japan

[73] Assignee: Kowa Co., Ltd., Nagoya, Japan

[21] Appl. No.: 464,345

[22] Filed: Jun. 5, 1995

[30] Foreign Application Priority Data

Jun. 27, 1994 [JP] Japan ................................. 6-144393

[51] Int. Cl.$^6$ ................................................. A01N 43/04
[52] U.S. Cl. ............................... 514/53; 514/54; 514/61; 424/667; 424/672; 424/78.06; 424/78.07
[58] Field of Search ................................ 514/53, 54, 61; 424/150, 80, 672, 667

[56] References Cited

U.S. PATENT DOCUMENTS

| | | | |
|---|---|---|---|
| 4,094,967 | 6/1978 | Gilbert | 424/28 |
| 4,844,898 | 7/1989 | Komori et al. | 424/150 |
| 4,950,653 | 8/1990 | Jauw | 514/53 |

FOREIGN PATENT DOCUMENTS

| | | |
|---|---|---|
| 0124774 | 11/1984 | European Pat. Off. . |
| 0196813 | 10/1986 | European Pat. Off. . |
| 0391852 | 10/1990 | European Pat. Off. . |
| 2353297 | 12/1977 | France . |
| 2048070 | 12/1980 | United Kingdom . |

*Primary Examiner*—Terressa Mosley
*Attorney, Agent, or Firm*—Oblon, Spivak, McClelland, Maier & Neustadt, P.C.

[57] ABSTRACT

A powder preparation for healing damaged skins, which comprises 50–90 wt. % of sucrose, 0.5–10 wt. % of povidone-iodine, and a water-soluble polymer selected from the group consisting of polyvinyl alcohol, polyvinyl pyrrolidone, polyacrylic acid and salts thereof, pullulan, carboxyvinyl polymers, methylcellulose, hydroxymethylcellulose, hydroxypropylmethylcellulose, and carboxymethylcellulose and salts thereof, is disclosed. The powder preparation features that it undergoes no caking even when vibrated upon its transportation or the like or stored for a long period of time, does not scatter upon its use, and has good adhesion to wound surfaces.

9 Claims, No Drawings

POWDER PREPARATION FOR HEALING DAMAGED SKIN

BACKGROUND OF THE INVENTION

1. Field of the Invention

The present invention relates to an external medicinal preparation useful for the healing of damaged skins such as burns or scalds, decubitus and open wounds, and more particularly to a powder preparation for healing damaged skins, which contains a sugar and povidone-iodine (polyvinyl pyrrolidone-iodine complex) as active ingredients.

2. Description of the Background Art

Sugars such as honey and molasses have conventionally been used, as folk medicine, for the treatment of burns or scalds and open wounds. These sugars have also been known to have bacteriostatic action and granulation tissue proliferating effects. Besides, povidone-iodine is a drug employed extremely widely as a bactericide throughout the world.

It has recently been reported that excellent effects of healing damaged skins were achieved when granulated sugar was mixed with a povidone-iodine preparation such as a Betadine ointment, Betadine solution, or Isodine gel (product of Meiji Seika Kaisha, Ltd.), and the resultant mixtures were applied to various damaged skins [R. A. Knutson et al., "Southern Medical Journal", Vol. 74, No. 11, 1329–1335 (1981); and Kiyokazu Sone et al., "Byoin Yakugaku (Hospital Pharmacology)", Vol. 10, No. 5, 315–322 (1984)].

However, the above-described compositions have involved problems that when stored at room temperature, they separate into two layers or change into the state like starch syrup, and moreover their active ingredients decompose to reduce the drug efficacy of the conposition. Therefore, they must have been stored in a cool and dark place. The active ingredients have however undergone decomposition in several months even when stored in this manner. It has been essential to prepare the compositions just before their use.

Studies have thus been conducted for overcoming such a disadvantage. As a result, in recent years, there has been developed an ointment preparation containing sucrose and povidone-iodine as active ingredients and having good long-term stability. Such an ointment preparation has been rated high by patients and the pharmacy interest in hospitals. However, there has been a demand for development of a preparation easy to use for applying to a wound surface rich in exudate or a deep wound, or to a granulation tissue surface easy to bleed, a patient having an acute pain or the like.

In view of the foregoing circumstances, a clinical experiment making use of a powder preparation, in which 3% of povidone-iodine powder was incorporated into sucrose, has been carried out ["Nichiidai-shi (Journal of Nippon Medical College)", Vol. 57, No. 2, 94 (1990)]. However, this powder preparation has involved a disadvantage that it undergoes a caking phenomenon during its storage for a long period of time or by vibrations upon its transportation due to the nature inherent in the sucrose amounting to 97% of the powder preparation, and so it can be neither taken out of a container nor spread to apply.

SUMMARY OF THE INVENTION

It is accordingly an object of the present invention to provide a powder preparation which contains sucrose and povidone-iodine and undergoes no caking even when stored for a long period of time.

In view of the foregoing circumstances, the present inventors have carried out an extensive investigation. As a result, it has been found that when a specific water-soluble polymer is incorporated into sucrose and povidone-iodine, a powder preparation, which undergoes no caking even when stored for a long period of time, shows excellent adhesion to a wound surface, does not scatter upon its application because it can be lumped by spreading it on gauze or the like and pressing it, and moreover can be easily removed by washing with water, can be obtained, thus leading to completion of the present invention.

In an aspect of the present invention, there is thus provided a powder preparation for healing damaged skins, which comprises (a) 50–90 wt. % of sucrose, (b) 0.5–10 wt. % of povidone-iodine, and (c) a water-soluble polymer selected from the group consisting of polyvinyl alcohol, polyvinyl pyrrolidone, polyacrylic acid and salts thereof, pullulan, carboxyvinyl polymers, methylcellulose, hydroxymethylcellulose, hydroxypropylmethylcellulose, and carboxymethylcellulose and salts thereof.

The powder preparation for healing damaged skins according to the present invention undergoes no caking even when vibrated upon its transportation or the like or stored for a long period of time, and moreover has excellent effects that it can be filled in a shaker for use, does not scatter upon its use and has good adhesion to wound surfaces.

The above and other objects, features and advantages of the present invention will become apparent from the following description and the appended claims.

DETAILED DESCRIPTION OF THE PREFERRED EMBODIMENTS

In order to obtain compositions of uniform quality in the present invention, it is particularly preferred that sucrose or purified sucrose specified in The Japanese Pharmacopoeia or the like be used as the sucrose (a). On the other hand, a polyvinyl pyrrolidone-iodine complex described in The Japanese Pharmacopoeia or the like is used as the povidone-iodine (b).

The amount of the sucrose (a) to be incorporated is 50–90 wt. % (hereinafter indicated merely by "%"), preferably 60–80% of the whole composition. The amount of the povidone-iodine (b) to be incorporated falls within a range of from 0.5%, the minimum proportion required for the exhibition of bacteriocidal action, to 10%.

In the present invention, the water-soluble polymer (c) serves to impart specific effects such as adhesion, prevention of scattering and prevention of caking to a preparation composed of sucrose and povidone-iodine. Such water-soluble polymers may be used either singly or in any combination of two or more polymers and incorporated in a proportion of 1–40%, preferably 4–20% of the whole composition.

Examples of particularly preferred water-soluble polymers include carboxyvinyl polymers and sodium carboxymethylcellulose.

In addition to these essential ingredients, a routinely used excipient, for example, a sugar alcohol (d) such as mannitol, maltitol, xylitol or sorbitol may be incorporated into the preparation according to the present invention as needed.

The amount of the sugar alcohol (d) if incorporated is preferably 10–30%, particularly 15–25% of the whole composition.

No particular limitation is imposed on the production process of the preparation according to the present invention. For example, it may be produced by grinding sucrose together with an excipient such as a sugar alcohol into fine powder by means of a high-speed mill or the like, adding povidone-iodine powder and a water-soluble polymer to this fine powder, and uniformly mixing the resultant mixture by means of a twin-cylinder mixer or the like. The thus-obtained powder preparation may be subjected to grading as needed.

The present invention will hereinafter be described in more detail by the following Examples.

EXAMPLE 1

|  | (parts by weight) |
|---|---|
| (1) Povidone-iodine | 3 |
| (2) Purified sucrose | 70 |
| (3) Sodium carboxymethylcellulose | 20 |
| (4) Carboxyvinyl polymer | 7 |

After the grain size of the ingredient (2) was adjusted by means of a high-speed mill, the ingredients (1), (3) and (4) were added thereto, and the resultant mixture was uniformly mixed in a mixer into a powder preparation.

This powder preparation showed a uniform powder state even after stored for 1 month at 50° C.

EXAMPLE 2

Powder preparations having their corresponding compositions shown in Table 1 were formulated in the same manner as in Example 1 to observe their properties after stored for 1 month at 50° C. The results are as shown in Table 1.

TABLE 1

| Ingredient (%) | Inventive product 1 | Inventive product 2 | Inventive product 3 | Inventive product 4 | Inventive product 5 | Inventive product 6 | Comparative product 1 | Comparative product 2 |
|---|---|---|---|---|---|---|---|---|
| Povidone-iodine | 7 | 3 | 1.5 | 5 | 3 | 3 | 3 | 3 |
| Sucrose | 70 | 90 | 50 | 60 | 70 | 80 | 97 | 70 |
| Mannitol | 18 | — | 33.5 | 30 | 20.5 | 7 | — | 27 |
| CMC-Na | — | — | 15 | 5 | 5 | — | — | — |
| CVP | — | 7 | — | — | 1.5 | — | — | — |
| PVP | — | — | — | — | — | 10 | — | — |
| PVA | 5 | — | — | — | — | — | — | — |
| Property | Powder | Powder | Powder | Powder | Powder | Powder | Caked | Caked |

Note)
CMC-Na: Sodium carboxymethylcellulose,
CVP: Carboxyvinyl polymer,
PVP: Polyvinyl pyrrolidone,
PVA: Polyvinyl alcohol.

EXAMPLE 3

Powder preparations having their corresponding compositions shown in Table 2 were formulated in the same manner as in Example 1 to observe their properties and appearance after stored for 1 month at 50° C. The results are as shown in Table 2.

TABLE 2

| Ingredient (%) | Inventive product 1 | Inventive product 2 | Comparative product 3 | Comparative product 4 | Comparative product 5 |
|---|---|---|---|---|---|
| Povidone-iodine | 7 | 3 | 3 | 3 | 3 |
| Sucrose | 70 | 90 | 87 | 87 | 87 |
| Mannitol | 18 | — | — | — | — |
| PVA | 5 | — | — | — | — |
| CVP | — | 7 | — | — | — |
| Pluronic F68 | — | — | 10 | — | — |
| Sucrose fatty acid ester | — | — | — | 10 | — |
| Polyethylene glycol 6000 | — | — | — | — | 10 |
| Property | Powder | Powder | Caked | Caked | Caked |
| Appearance | Not changed | Not changed | Blackened | Not changed | Yellowed |

Note)
PVA: Polyvinyl alcohol,
CVP: Carboxyvinyl polymer,
Pluronic F68: Poly(oxyethylene) [160] poly(oxypropylene) [30] glycol.

What is claimed is:

1. A composition, consisting essentially of:
   (a) 50–90 wt. % of sucrose;
   (b) 0.5–10 wt. % of povidone-iodine powder; and
   (c) a water-soluble polymer selected from the group consisting of polyvinyl alcohol, polyvinyl pyrrolidone, polyacrylic acid and salts thereof, pullulan, carboxyvinyl polymers, methylcellulose, hydroxymethylcellulose, hydroxypropylmethylcellulose, and carboxymethylcellulose and salts thereof,
   wherein said composition is a powder.

2. The powder preparation according to claim 1, wherein the water-soluble polymer (c) is contained in an amount of 1–40 wt. % of the whole composition.

3. The powder preparation according to claim 1, further comprising (d) a sugar alcohol.

4. The powder preparation according to claim 3, wherein the sugar alcohol is contained in an amount of 10–30% of the whole composition.

5. The composition according to claim 1, wherein said water-soluble polymer is selected from the group consisting of polyvinyl alcohol, polyacrylic acid and salts thereof and carboxyvinyl polymers.

6. The composition according to claim 1, wherein said composition remains a powder after storage for one month at 50° C.

7. A composition, consisting of:
   (a) 50–90 wt. % of sucrose;
   (b) 0.5–10 wt. % of povidone-iodine powder; and
   (c) a water-soluble polymer selected from the group consisting of polyvinyl alcohol, polyvinyl pyrrolidone, polyacrylic acid and salts thereof, pullulan, carboxyvinyl polymers and methylcellulose;
   wherein said composition is a powder.

8. The composition according to claim 6, wherein said water-soluble polymer is selected from the group consisting of polyvinyl alcohol, polyacrylic acid and salts thereof and carboxyvinyl polymers.

9. The composition according to claim 7, wherein said composition remains a powder after storage for one month at 50° C.

* * * * *